US00PP13673P29

(12) United States Plant Patent
Sinning

(10) Patent No.: US PP13,673 P2
(45) Date of Patent: Mar. 25, 2003

(54) AGASTACHE PLANT NAMED 'SINNING'

(76) Inventor: Duane Sinning, 3840 Ash Ave., Loveland, CO (US) 80538-2171

( * ) Notice: Subject to any disclaimer, the term of this patent is extended or adjusted under 35 U.S.C. 154(b) by 0 days.

(21) Appl. No.: 10/171,828

(22) Filed: Jun. 17, 2002

(51) Int. Cl.[7] ..... A01H 5/00

(52) U.S. Cl. ..... Plt./258; Plt./263

(58) Field of Search ..... Plt./258, 263

(56) References Cited

PUBLICATIONS

Brown, Deni. The Herb Society of America Encyclopedia of Herbs and Their Uses. DK Publishing, Inc. New York, New York, 1995, p. 75.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Agastache plant named 'Sinning', characterized by its uniform, compact and upright plant habit; freely branching growth habit; early flowering; numerous purple-colored tubular flowers positioned close together on erect flowering spikes; fragrant foliage and flowers; and excellent garden performance.

1 Drawing Sheet

BOTANICAL CLASSIFICATION/CULTIVAR DESIGNATION

*Agastache cana* cultivar Sinning.

BACKGROUND OF THE INVENTION

The present Invention relates to a new and distinct cultivar of Agastache plant, botanically known as *Agastache cana*, commercially known as Hyssop, and hereinafter referred to by the name 'Sinning'.

The new Agastache is a product of a planned breeding program conducted by the Inventor in Denver, Colo. The objective of the breeding program is to create new Agastaches with improved plant habit and flowering characteristics.

The new Agastache originated from a cross made by the Inventor in August, 1999 of an unnamed proprietary seedling selection of *Agastache cana*, not patented, as the female, or seed parent, with an unnamed proprietary seedling selection of *Agastache cana*, not patented, as the male, or pollen parent. The new Agastache was selected as a single plant from the resulting progeny by the Inventor in a controlled environment in Denver, Colo., on the basis of its uniform plant and flowering habit in August, 1999.

Asexual reproduction of the new cultivar by cuttings taken in a controlled environment in Denver, Colo. since September, 1999, has shown that the unique features of this new Agastache are stable and reproduced true to type in successive generations.

SUMMARY OF THE INVENTION

Plants of the cultivar Sinning have not been observed under all possible environmental conditions. The phenotype may vary somewhat with variations in environment and culture such as temperature, light intensity, and daylength without, however, any variance in genotype.

The following traits have been repeatedly observed and are determined to be the unique characteristics of 'Sinning'.

These characteristics in combination distinguish 'Sinning' as a new and distinct cultivar:

1. Uniform, compact and upright plant habit.
2. Freely branching growth habit.
3. Early flowering.
4. Numerous purple-colored tubular flowers positioned close together on erect flowering spikes.
5. Fragrant foliage and flowers.
6. Excellent garden performance.

In side-by-side comparisons conducted in Denver, Colo., plants of the new Agastache differed from plants of the female parent selection in the following characteristics:

1. Plants of the new Agastache were more compact and not as vigorous as plants of the female parent.
2. Plants of the new Agastache had more uniform branching than plants of the female parent.
3. Inflorescences of plants of the new Agastache were more compact and had more flowers per length of flowering spike than inflorescences of plants of the female parent.
4. Foliage and flowers of plants of the new Agastache were more fragrant than foliage and flowers of plants of the female parent.

In side-by-side comparisons conducted in Denver, Colo., plants of the new Agastache differed from plants of the male parent selection in the following characteristics:

1. Plants of the new Agastache were more compact and not as vigorous as plants of the male parent.
2. Plants of the new Agastache had stronger lateral branches than plants of the male parent.
3. Inflorescences of plants of the new Agastache were more compact and had more flowers per length of flowering spike than inflorescences of plants of the male parent.
4. Foliage and flowers of plants of the new Agastache were more fragrant than foliage and flowers of plants of the male parent.

Plants of the new Agastache can be compared to plants of the cultivar Heather Queen, not patented. In side-by-side comparisons conducted in Denver, Colo., plants of the new Agastache and the cultivar Heather Queen differed in the following characteristics:

1. Plants of the new Agastache were more compact and not as vigorous as plants of the cultivar Heather Queen.

2. Plants of the new Agastache had more uniform branching than plants of the cultivar Heather Queen.

3. Leaves of plants of the new Agastache had lighter green-colored upper surfaces and less purple coloration on the lower surfaces than plants of the cultivar Heather Queen.

4. Inflorescences of plants of the new Agastache were more compact and had more flowers per length of flowering spike than inflorescences of plants of the cultivar Heather Queen.

5. Foliage and flowers of plants of the new Agastache were much more fragrant than foliage and flowers of plants of the cultivar Heather Queen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Agastache.

The photograph at the top of the sheet comprises a side perspective view of a typical flowering plant of 'Sinning'.

The photograph at the bottom of the sheet comprises a close-up view of a typical flowering plant of 'Sinning' showing the foliage and flowers.

DETAILED BOTANICAL DESCRIPTION

Plants used for the aforementioned photographs and following observations and measurements were planted into 11.5-cm containers in April, 2001 and grown for about 22 weeks in a polyethylene-covered greenhouse in Denver, Colo. During the production of the plants, the day temperatures ranged from 20 to 26° C. and night temperatures ranged from 18 to 22° C.

In the following description, color references are made to The Royal Horticultural Society Colour Chart except where general terms of ordinary dictionary significance are used.

Botanical classification: *Agastache cana* cultivar Sinning.

Parentage:

*Female, or seed, parent.*—Unnamed proprietary seedling selection of *Agastache cana*, not patented.

*Male, or pollen, parent.*—Unnamed proprietary seedling selection of *Agastache cana*, not patented.

Propagation:

*Type cutting.*—Stem and terminal cuttings are both used.

*Time to initiate roots.*—Summer: About 14 days at 24° C. Winter: About 18 days at 24° C.

*Time to develop roots.*—Summer: About 21 to 28 days at 24° C. Winter: About 28 to 35 days at 24° C.

*Root description.*—Fine, freely branching.

Plant description:

*Form.*—Upright, uniform and compact. Perennial. Freely branching with about six primary lateral branches; lateral branches potentially forming at every node. Moderately vigorous growth habit.

*Plant height.*—About 40 cm.

*Plant diameter.*—About 38 cm.

*Lateral branches.*—Length: About 37 cm. Diameter: About 3.25 mm. Internode length: About 2.5 cm. Strength: Moderately strong. Texture: Fine pubescence. Cross-section: Square. Color: 144A to 146A.

*Foliage description.*—Arrangement: Opposite, simple. Length: About 3.9 cm. Width: About 3 cm. Shape: Ovate with deltoid tendencies. Apex: Acute. Base: Truncate to cordate. Margin: Entire to crenate. Orientation: Mostly horizontal. Aspect: Mostly flat. Texture: Glabrous. Venation pattern: Pinnate, arcuate. Fragrance: Aromatic, sweetly pungent. Petiole length: About 1.75 cm. Petiole diameter: About 1 mm. Color: Young foliage, upper surface: 147A. Young foliage, lower surface: Close to 146A. Fully expanded foliage, upper surface: Close to 147A. Fully expanded foliage, lower surface: Close to, but darker than 147B. Venation, upper surface: Close to 147A. Venation, lower surface: Close to 147B. Petiole, upper and lower surfaces: Close to 146A.

Flower description:

*Flower type and habit.*—Numerous single bilabiate flowers arranged in verticillasters arranged in terminal and axillary spikes. Individual flowers face mostly outward. Freely flowering with more than 25 flowers and flower buds per spike, about 5 to 9 spikes per lateral branch. Flowers not persistent.

*Time to flower.*—Early flowering, plants begin to flower about 12 to 16 weeks after planting.

*Natural flowering season.*—In the northern hemisphere, plants flower from mid-June through September, flowering continuous during this period.

*Flower longevity on the plant.*—About one week.

*Fragrance.*—Aromatic, sweetly pungent.

*Terminal spike height.*—About 6.5 cm.

*Terminal spike diameter.*—About 6 cm.

*Flowers.*—Appearance: Zygomorphic; bilabiate. Length: About 1.6 cm. Diameter: About 1 cm. Depth: About 3.2 cm.

*Flower buds (showing color).*—Length: About 1 cm. Diameter: About 2.5 mm. Shape: Elongated oblong. Color: 4D overlain with 72A to 72B.

*Corolla.*—Petal arrangement/appearance: Bilabiate; five petals, upper two petals fused and lower three petals fused, all five petals fused at base into a tubular structure. Petal length: Upper petals: About 3.2 cm. Lower petals: About 3.1 cm. Petal width: Upper petals: About 5.5 mm. Lower petals: About 1 cm. Petal apex: Rounded to crenate. Petal margin: Entire to crenate. Petal texture: Smooth, satiny. Petal color: When opening, upper and lower surfaces: 59A. Fully opened, upper surface: 74A fading to 78A with subsequent development. Fully opened, throat: 155D overlain with 74A fading to 77A with subsequent development. Fully opened, lower surface and tube: 71A fading to 72B to 78A with subsequent development.

*Calyx.*—Quantity/arrangement: One single calyx tube per flower; five fused sepals. Length: About 1.4 cm. Diameter: Apex: About 5 mm. Base: About 3.5 mm. Shape: Tubular or cup-shaped. Apex: Sharply acuminate. Texture, upper and lower surfaces: Slightly pubescent. Color: Immature, upper and lower surfaces: Close to 4D. Mature, upper surface: Close to 4D overlain with 71A to 72A. Mature, lower surface: Close to 4D overlain with 72A to 72B.

*Peduncles.*—Length: About 6.5 cm. Diameter: About 1.5 mm. Strength: Strong. Angle: Terminals, erect;

axillary, about 45° from vertical. Texture: Fine pubescence. Color: 144A to 146A.

*Pedicels.*—Length: About 7 mm. Diameter: Less than 1 mm. Strength: Moderately strong. Angle: Terminals, erect; axillary, about 45° from vertical. Texture: Fine pubescence. Color: 144A overlain with 58A towards the flower.

*Reproductive organs.*—Stamens: Quantity per flower: Four, adnate to the petals. Stamen length: About 3.5 cm. Filament color: Close to 77B. Anther shape: Bi-lobed. Anther length: About 1 mm. Anther color: Close to 79A. Pollen amount: Scarce. Pollen color: Close to 4D. Pistils: Quantity per flower: One. Pistil length: About 3.4 cm. Style color: Towards base, 155D; towards apex, 77B. Stigma shape: Forked. Stigma color: Close to 71A. Ovary color: 144A.

*Seed/fruit.*—Seed nor fruit production have not been observed.

Disease/pest resistance: Plants of the new Agastache have not been noted to be resistant to pathogens or pests common to Agastache.

Weather tolerance: Plants of the new Agastache have been observed to be tolerant to rain, wind and temperatures ranging from −15 to 51° C.

It is claimed:

1. A new and distinct cultivar of Agastache plant named 'Sinning', as illustrated and described.

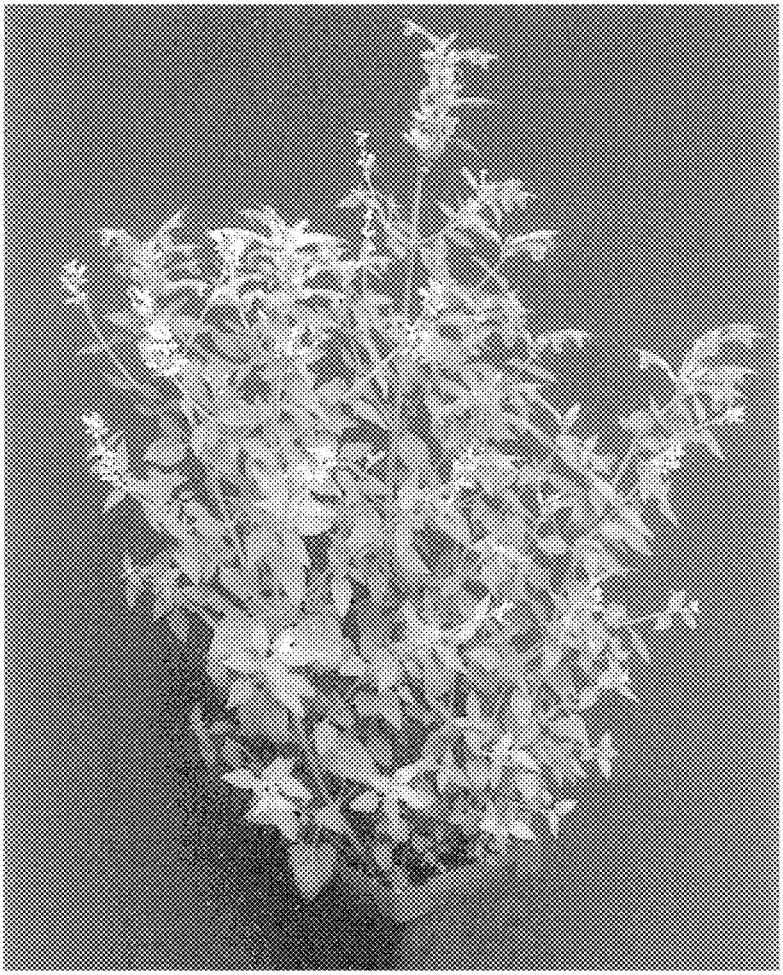
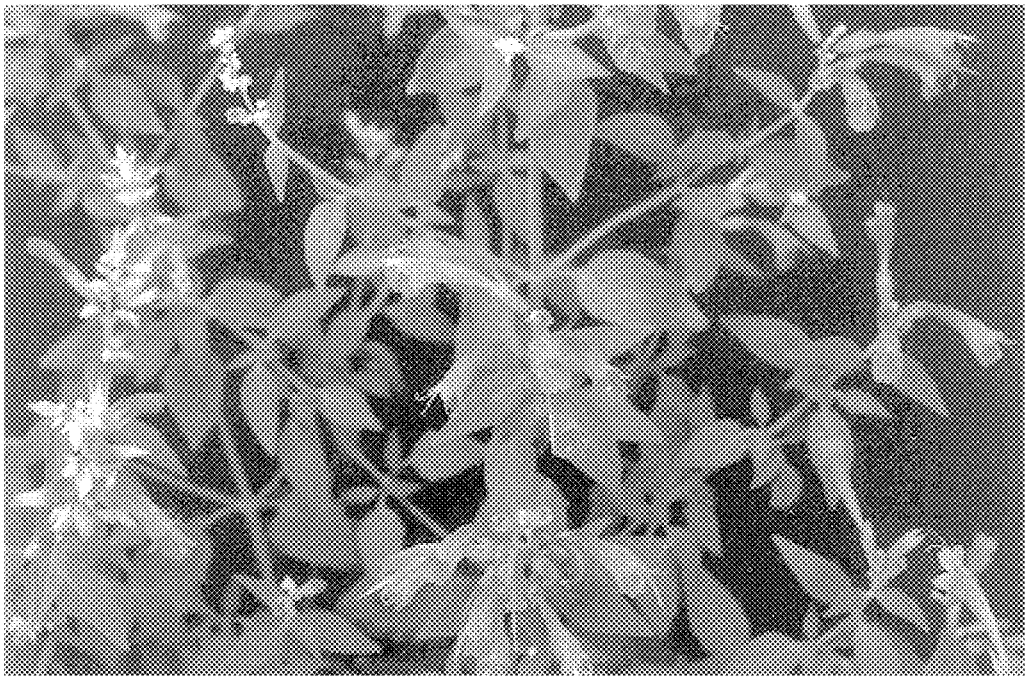

* * * * *